US012584159B2

(12) United States Patent
Berthelette

(10) Patent No.: US 12,584,159 B2
(45) Date of Patent: Mar. 24, 2026

(54) SEPARATION OF NUCLEIC ACID COMPONENT COMPOUNDS ON ZWITTERIONIC STATIONARY PHASES

(71) Applicant: Waters Technologies Corporation, Milford, MA (US)

(72) Inventor: Kenneth Berthelette, Millville, MA (US)

(73) Assignee: Waters Technologies Corporation, Milford, MA (US)

( * ) Notice: Subject to any disclaimer, the term of this patent is extended or adjusted under 35 U.S.C. 154(b) by 965 days.

(21) Appl. No.: 17/831,641

(22) Filed: Jun. 3, 2022

(65) Prior Publication Data

US 2022/0389480 A1 Dec. 8, 2022

Related U.S. Application Data

(60) Provisional application No. 63/196,788, filed on Jun. 4, 2021.

(51) Int. Cl.

| | |
|---|---|
| ***C12Q 1/68*** | (2018.01) |
| ***C12Q 1/6806*** | (2018.01) |
| ***G01N 30/72*** | (2006.01) |
| *G01N 30/02* | (2006.01) |

(52) U.S. Cl.

CPC ............. *C12Q 1/68* (2013.01); *C12Q 1/6806* (2013.01); *G01N 30/7233* (2013.01); *G01N 2030/027* (2013.01)

(58) Field of Classification Search

CPC ........................................................ C12Q 1/68

See application file for complete search history.

(56) References Cited

U.S. PATENT DOCUMENTS

| | | | | |
|---|---|---|---|---|
| 2014/0021136 A1* | 1/2014 | Qiu | B01J 20/288 521/53 |
| 2017/0203234 A1* | 7/2017 | Armstrong | B01J 20/24 |

OTHER PUBLICATIONS

Marrubini et al., J. Sep. Science 33, 803-816 (2010). (Year: 2010).*

International Search Report and Written Opinion issued in International Patent Application No. PCT/IB2022/055204 dated Sep. 5, 2022.

Rodriguez-Gonzalo et al. "Study of retention behavious and mass spectrometry compatibility in zwitterionic hydrophilic interaction chromatography for the separation of modified nucleosides and nucleobases." J. Chromatogr. A. 1218 (2011): 3994-4001.

Salas et al. "Hydrophilic interaction liquid chromatography coupled to mass spectrometry-based detection to determine emerging organic contaminants in environmental samples." Trends Anal. Chem. 94(2017): 141-149.

Taraji et al. "Chemometric-assisted method development in hydrophilic interaction liquid chromatography: A review." Anal. Chim. Acta. 1000(2018): 20-40.

* cited by examiner

*Primary Examiner* — Kenneth R Horlick

(74) *Attorney, Agent, or Firm* — WOMBLE BOND DICKINSON (US) LLP; Deborah M. Vernon; Ricardo Joseph

(57) ABSTRACT

The present disclosure pertains to methods of separating nucleic acid component compounds from one another. In some embodiments, the methods comprise: (a) loading a sample fluid comprising a plurality of nucleic acid component compounds onto a chromatographic column comprising a zwitterionic stationary phase contained inside the column; (b) flowing a mobile phase through the chromatographic column over a time period thereby forming an eluent in which at least some of the plurality of the nucleic acid component compounds are separated from each other, the mobile phase comprising a polar aprotic solvent, a protic solvent, and a volatile buffer salt, wherein flowing the mobile phase comprises varying a ratio of the protic solvent to the polar aprotic solvent over at least a portion of the time period and varying an ionic strength of the volatile buffer salt over at least a portion of the time period.

19 Claims, 2 Drawing Sheets

SEPARATION OF NUCLEIC ACID COMPONENT COMPOUNDS ON ZWITTERIONIC STATIONARY PHASES

CROSS-REFERENCE TO RELATED APPLICATIONS

This application claims priority to and the benefit of U.S. Provisional Application No. 63/196,788 filed Jun. 4, 2021; which contents are incorporated herein by reference in their entirety.

FIELD OF THE TECHNOLOGY

In various aspects, the present disclosure pertains to the separation of nucleic acid component compounds in sample fluids from one another on zwitterionic stationary phases.

BACKGROUND

Ribonucleic acid (RNA) is a polymeric molecule essential in various biological roles in coding, decoding, regulation and expression of genes. Ribonucleic Acid (RNA) is formed from chains of nucleotides joined by phosphodiester bonds between the 3'-hydroxyl group of one pentose and the 5'-hydroxyl group of an adjacent pentose. RNA is generally comprised of four different types of nucleotides. These nucleotides are comprised of three component compounds: a) a nucleobase, b) D-ribose, and c) a phosphate group. The nucleobases are generally from two N-heterocyclic categories, namely pyrimidine and purine. The two purine-type bases are adenine (A),

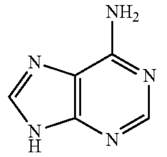

and guanine (G),

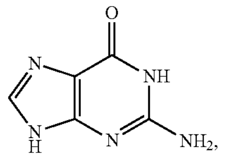 [SMILES: Nc1nc2[nH]cnc2c(=O)[nH]1]

and the two pyrimidine-type bases are cytosine (C),

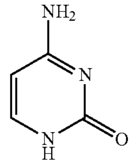

and uracil (U)

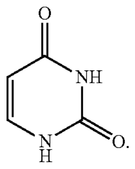

The combination of D-ribose and base is called a nucleoside and these include adenosine,

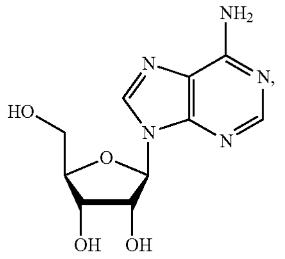

guanosine,

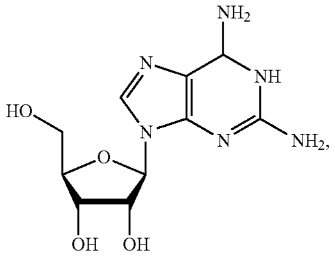

cytidine,

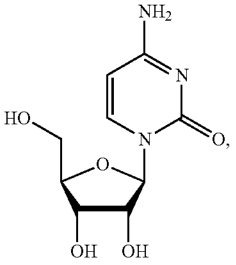

and uridine,

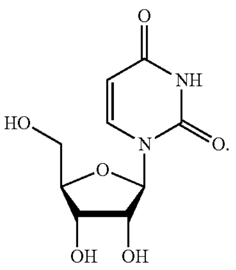

A nucleotide may also be called a "nucleoside phosphate" such as a "nucleoside monophosphate", a "nucleoside diphosphate" or a "nucleoside triphosphate", depending on how many phosphate units make up the phosphate group. Nucleoside monophosphates include, adenosine monophosphate,

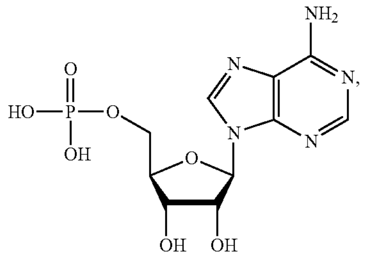

guanosine monophosphate,

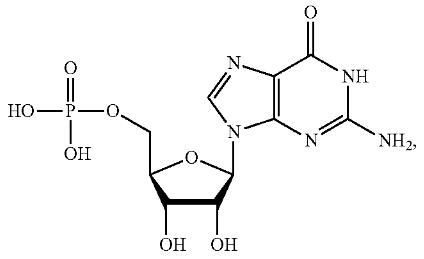

cytidine monophosphate,

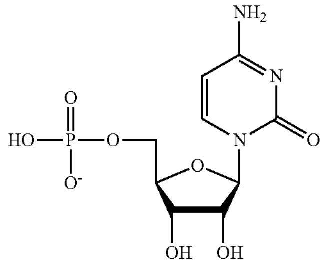

and uridine monophosphate,

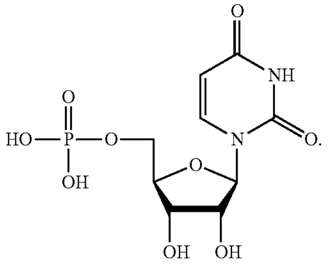

In the form of nucleoside triphosphates (e.g., adenosine triphosphate (ATP), guanosine triphosphate (GTP), cytidine triphosphate (CTP) and uridine triphosphate (UTP)), nucleotides also play a role in metabolism.

Another important phosphate is ribose 5-phosphate,

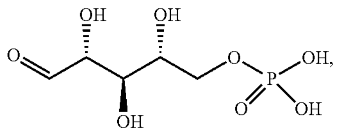 [SMILES: O=C[C@H](O)[C@H](O)[C@H](O)COP(=O)(O)O]

which is a product and an intermediate of the pentose phosphate pathway, a metabolic pathway that is a crucial source for NADPH generation for reductive biosynthesis.

The analysis of these components are critical for many areas of study including but not limited to disease monitoring, metabolomic pathway analysis, and nutrient monitoring of consumer products.

SUMMARY

In various aspects, the present disclosure pertains to the separation of nucleic acid component compounds in sample fluids from one another.

In some embodiments, the present disclosure pertains to methods that comprise: (a) loading a sample fluid comprising a plurality of nucleic acid component compounds onto a chromatographic column comprising a zwitterionic stationary phase contained inside the column; (b) flowing a mobile phase through the chromatographic column over a time period thereby forming an eluent in which at least some of the plurality of the nucleic acid component compounds are separated from each other, the mobile phase comprising a polar aprotic solvent, a protic solvent, and a volatile buffer salt, wherein flowing the mobile phase comprises varying a ratio of the protic solvent to the polar aprotic solvent over at least a portion of the time period and varying an ionic strength of the volatile buffer salt over at least a portion of the time period.

In some embodiments, the methods further comprise performing mass spectrometry analysis of the eluent. Mass spectrometry analysis may be performed, for example, in positive ion mode, in negative ion mode, or both.

In some embodiments, which can be used in conjunction with the preceding embodiments, the zwitterionic stationary phase is a particulate stationary phase.

In some embodiments, which can be used in conjunction with the preceding embodiments, the zwitterionic stationary phase comprises (i) a bulk material and (ii) zwitterionic surface groups covalently linked to the bulk material, the zwitterionic surface groups comprising a positively charged moiety and a negatively charged moiety.

In some embodiments, which can be used in conjunction with the preceding embodiments, the zwitterionic stationary phase comprises a bulk material and a zwitterionic polymer covalently linked to a surface of the bulk material, the zwitterionic polymer comprising one or more monomer residues that comprise an amide or urea moiety, a positively charged moiety and a negatively charged moiety.

In some embodiments, which can be used in conjunction with the preceding embodiments, the positively charged moiety is a quaternary ammonium moiety and the negatively charged moiety is selected from a sulfate moiety, a sulfonate moiety, a phosphate moiety or a phosphonate moiety.

In some embodiments, which can be used in conjunction with the preceding embodiments, an inner surface of the chromatographic column comprises a $(C_2\text{-}C_{10})$alkylsilyl coating.

In some embodiments, which can be used in conjunction with the preceding embodiments, the nucleic acid component compounds comprise RNA component compounds. For example, the RNA component compounds may be selected from nucleobases, nucleosides, nucleotides and ribose phosphate.

In some embodiments, which can be used in conjunction with the preceding embodiments, the protic solvent is selected from water, methanol, ethanol, 1-propanol, 2-propanol, t-butanol and blends thereof.

In some embodiments, which can be used in conjunction with the preceding embodiments, the polar aprotic solvent is selected from acetonitrile, acetone, tetrahydrofuran, methylene chloride, ethyl acetate, N,N-dimethylformamide, dimethyl sulfoxide, dimethyl ether, and blends thereof.

In some embodiments, which can be used in conjunction with the preceding embodiments, the volatile buffer salt comprises an organic acid anion and a cation selected from an ammonium cation and an amine cation. For example, the organic acid anion may be selected from formate, acetate, propionate, butyrate, oxalate, malonate, succinate, maleate, glutarate, glycolate, lactate, malate, citrate, gluconate and combinations thereof, and the cation may be selected from an ammonium cation, a methyl ammonium cation, a methyl diammonium cation, an ethyl ammonium cation, a ethyl diammonium cation, a diethyl ammonium cation, a diethanol ammonium cation, a tromethamine cation, a choline cation, a pyrrolidinium cation, a pyrrolium cation, a piperazinium cation, a pyridinium cation and combinations thereof.

In some embodiments, which can be used in conjunction with the preceding embodiments, flowing the mobile phase comprises combining varying relative amounts of (a) a first mobile phase component comprising an aqueous solution of the volatile buffer salt and (b) a second mobile phase component comprising the polar aprotic solvent.

In some embodiments, which can be used in conjunction with the preceding embodiments, flowing the mobile phase comprises combining varying relative amounts of (a) a first mobile phase component comprising an aqueous solution of the volatile buffer salt, (b) a second mobile phase component comprising the polar aprotic solvent, and (c) a third mobile phase component comprising the protic solvent.

In some embodiments, which can be used in conjunction with the preceding embodiments, the first mobile phase component has a pH ranging from 2.0 to 4.0.

In some embodiments, which can be used in conjunction with the preceding embodiments, the sample fluid comprises the plurality of nucleic acid component compounds, a protic solvent, a polar aprotic solvent, and an organic acid. In particular embodiments, the sample fluid comprises the plurality of nucleic acid component compounds, water, acetonitrile and formic acid.

BRIEF DESCRIPTION OF DRAWINGS

FIG. 1A is the chromatogram from the separation on a column with BEH amide particles; FIG. 1B is the chromatogram from the separation on a column with modified BEH particles (e.g., Example 1); FIG. 1C is the chromatogram from the separation on a column with Raptor Polar particles; and FIG. 1D is the chromatogram from the separation on a column with Poroshell HILIC-z particles FIG. 2A is the chromatogram from the separation on a column with BEH amide particles; FIG. 2B is the chromatogram from the separation on a column with modified BEH particles (e.g., Example 1); FIG. 2C is the chromatogram from the separation on a column with Raptor Polar particles; and FIG. 2D is the chromatogram from the separation on a column with Poroshell HILIC-z particles

DETAILED DESCRIPTION

Figure 1A:
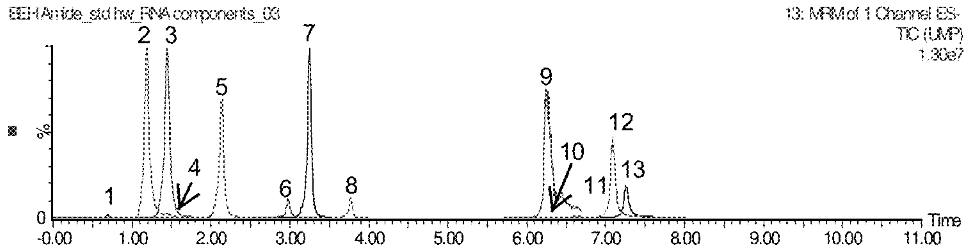
FIGS. 1A-1D are chromatograms corresponding to attempted separations of thirteen different RNA component compounds in a sample, using four different zwitterionic columns, wherein the Y-axes of the chromatograms are linked. Each compound (Uracil, Adenine, Adenosine, Uridine, Cytosine, Guanine, Cytidine, Guanosine, AMP, UMP, Ribose phosphate, CMP and GMP) is assigned to a peak number (1, 2, 3, 4, 5, 6, 7, 8, 9, 10, 11, 12 and 13) respectively.

In various aspects, the present disclosure pertains to methods of separating nucleic acid component compounds in sample fluids from one another.

Such nucleic acid component compounds may include RNA component compounds and DNA component compounds. Particular RNA nucleic acid component compounds include RNA nucleobases, specifically, adenine, guanine, cytosine and uracil, RNA nucleosides, specifically, adenosine, guanosine, cytidine and uridine, RNA nucleotides including nucleoside monophosphates, nucleoside diphosphates and nucleoside triphosphates, such as adenosine monophosphate, guanosine monophosphate, cytidine monophosphate, uridine monophosphate, adenosine diphosphate, guanosine diphosphate, cytidine diphosphate, uridine diphosphate, adenosine triphosphate, guanosine triphosphate, cytidine triphosphate and uridine triphosphate, and ribose 5-phosphate.

Sample fluids for use in the methods of the present disclosure include those derived from biological fluids and include whole blood samples, blood plasma samples, serum samples, oral fluids, cerebrospinal fluids, fecal samples, nasal samples, urine, biological tissues such as liver, kidney and brain tissue, tissue homogenates, cells, cell culture supernatants, and food matrices such as infant formula, among others. Prior to separation, such samples may be pretreated as described further below.

In various aspects, the methods of the present disclosure comprise: (a) loading a sample fluid comprising a plurality of nucleic acid component compounds onto a chromatographic column comprising a zwitterionic stationary phase contained inside the column; (b) flowing a mobile phase through the chromatographic column over a time period thereby forming an eluent in which at least some of the plurality of the nucleic acid component compounds are separated from each other. The mobile phase comprises a polar aprotic solvent, a protic solvent, and a volatile buffer salt. The process of flowing the mobile phase through the chromatographic column comprises varying a ratio of the protic solvent to the polar aprotic solvent over at least a portion of the time period and varying an ionic strength of the volatile buffer salt over at least a portion of the time period.

In various embodiments, the methods of the present disclosure further comprise additional processing of the eluent from the chromatographic column, for example, to identify, quantify, or otherwise process the nucleic acid component compounds. In certain beneficial embodiments, mass spectrometry (MS) analysis is performed on the eluent. Particular examples of mass spectrometry include electrospray ionization mass spectrometry (ESI-MS), matrix-assisted laser desorption/ionization mass spectrometry (MALDI-MS), and time-of-flight mass spectrometry (TOFMS), among others. Alternatively, or in addition, the eluent may be subjected to other analytical techniques including fluorescence analysis, infrared analysis, ultraviolet analysis, and nuclear magnetic resonance analysis, among others.

In some embodiments, the protic solvent employed in mobile phase is selected from water, methanol, ethanol, 1-propanol, 2-propanol, t-butanol and blends thereof. In particular embodiments, the protic solvent is water.

In some embodiments, the polar aprotic solvent employed in the mobile phase is selected from acetonitrile, acetone, tetrahydrofuran, methylene chloride, ethyl acetate, N,N-dimethylformamide, dimethyl sulfoxide, dimethyl ether, and blends thereof. In particular embodiments, the polar aprotic solvent is acetonitrile.

In some embodiments, the volume % of the protic solvent in the mobile phase increases over time. In some embodiments, the volume % of the protic solvent in the mobile phase decreases over time. In certain embodiments, the volume % of the protic solvent in the mobile phase increases over time and decreases over time. In some embodiments, a first volume % of the protic solvent in the mobile phase is between 3 and 7 volume % at a first point in time, a second volume % of the protic solvent in the mobile phase may be between 35 and 45 volume % at a second point in time, and a third volume % of the protic solvent in the mobile phase may be between 3 and 5 volume % at a third point in time. In certain embodiments, a rate of change in the mobile phase the protic solvent ranges from 3 to 4 vol %/minute during at least a portion of the period of time.

In some embodiments, the volume % of the polar aprotic solvent in the mobile phase decreases over time. In certain embodiments, the volume % of the polar aprotic solvent in the mobile phase decreases over time and then increases over time. In some embodiments, the volume % of the polar aprotic solvent in the mobile phase decreases over time and increases over time. In some embodiments, a first volume % of the polar aprotic solvent in the mobile phase is between 93 and 97 volume % at a first point in time, a second volume % of the polar aprotic solvent in the mobile phase may be between 55 and 65 volume % at a second point in time, and a third volume % of the polar aprotic solvent in the mobile phase may be between 93 and 97 volume % at a third point in time. In certain embodiments, a rate of change in the mobile phase the polar aprotic solvent ranges from 3 to 4 vol %/minute during at least a portion of said period of time.

In some embodiments, the volatile buffer salt employed in the mobile phase comprises an organic acid anion and a cation selected from an ammonium cation and an amine cation. In certain embodiments, the organic acid anion is selected from formate, acetate, propionate, butyrate, oxalate, malonate, succinate, maleate, glutarate, glycolate, lactate, malate, citrate, gluconate and combinations thereof. In certain embodiments, the amine cation is selected from an ammonium cation, a methyl ammonium cation, a methyl diammonium cation, an ethyl ammonium cation, a ethyl diammonium cation, a diethyl ammonium cation, a diethanol ammonium cation, a tromethamine cation, a choline cation, a pyrrolidinium cation, a pyrrolium cation, a piperazinium cation, a pyridinium cation and combinations thereof.

The ionic strength of the volatile buffer salt in the mobile phase solution may vary widely. Ionic strength is expressed by the equation, $$I = \frac{1}{2}\sum_i c_i z_i^2,$$

where $c_i$ is the molar concentration of any ion in solution, and $z_i$ is its valence. For salts consisting of an anion having a valence of 1 and a cation having a valence of 1, the ionic strength of the solution is equal to the molar concentration of the dissolved salt.

In some embodiments, the ionic strength of the volatile buffer salt in the mobile phase increases over time. In some embodiments, the ionic strength of the volatile buffer salt in the mobile phase decreases over time. In some embodiments, the ionic strength of the volatile buffer salt in the mobile phase increases over time and then decreases over time. In certain embodiments, a first ionic strength of the volatile buffer salt in the mobile phase is between 7 and 13 mM at a first point in time, a second ionic strength of the volatile buffer salt in the mobile phase may be between 45 and 55 mM at a second point in time, and a third ionic strength of the volatile buffer salt in the mobile phase may be between 7 and 13 mM at a third point in time. In certain embodiments, a rate of change the ionic strength of the volatile buffer salt in the mobile phase ranges from 3 to 4 mM/minute during at least a portion of said period of time.

In some embodiments, the process of flowing the mobile phase in the methods of the present disclosure comprises combining varying relative amounts of (a) a first mobile phase component comprising an aqueous solution of the volatile buffer salt and (b) a second mobile phase component comprising the polar aprotic solvent. In some embodiments, flowing the mobile phase comprises combining varying relative amounts of (a) a first mobile phase component comprising an aqueous solution of the volatile buffer salt, (b) a second mobile phase component comprising the polar aprotic solvent, and (c) a third mobile phase component comprising the protic solvent.

In some embodiments, the first mobile phase component has a pH ranging from 2.0 to 4.0.

As previously noted, in various embodiments, the methods of the present disclosure further comprise additional processing of the eluent, for example, to identify, quantify, or otherwise process the nucleic acid component compounds. In some beneficial embodiments, mass spectrometry analysis is performed the eluent.

In certain embodiments, for example, where mass spectrometry analysis is performed the eluent and where the mass spectrometer is operated in positive ion mode. In certain embodiments, for example, where mass spectrometry analysis is performed the eluent and where the mass spectrometer is operated in negative ion mode.

In some embodiments, the sample fluid comprises the plurality of nucleic acid component compounds, a protic solvent, a polar aprotic solvent, and a volatile acid. In some embodiments, the protic solvent and the polar aprotic solvent may be selected from those described above. In some embodiments, the protic solvent is acetonitrile and the polar aprotic solvent is water. In some embodiments, an amount of polar aprotic solvent in the sample fluid ranges from 80 to 90 vol %. In some embodiments, an amount of the nucleic acid compound components in the sample fluid ranges from 2.0 to 50 μg/mL In some embodiments, the volatile acid in the sample fluid is an organic acid. In some embodiments, the organic acid may be selected from formic acid, acetic acid, difluoroacetic acid, trifluoroacetic acid, propionic acid, butyric acid, oxalic acid, malonic acid, succinic acid, maleic acid, glutaric acid, and organic hydroxyacids such as glycolic acid, lactic acid, tartaric acid, malic acid, citric acid and gluconic acid, among others. In some embodiments, a concentration of the volatile acid in the sample fluid ranges from 190 to 210 mM.

In some embodiments, the sample fluid comprises the plurality of nucleic acid component compounds, water, acetonitrile and formic acid.

As previously noted, in various aspects, the methods of the present disclosure comprise: (a) loading a sample fluid comprising a plurality of nucleic acid component compounds onto a chromatographic column comprising a zwitterionic stationary phase contained inside the column and (b) flowing a mobile phase through the chromatographic column over a time period thereby forming an eluent in which at least some of the plurality of the nucleic acid component compounds are separated from each other.

In some embodiments, the zwitterionic stationary phase in the chromatographic column comprises (i) a bulk material and (ii) zwitterionic surface groups that are adsorbed to or covalently linked to the bulk material. Being zwitterionic, the zwitterionic surface groups comprise a positively charged moiety and a negatively charged moiety. Various bulk materials and zwitterionic surface groups are described in detail below.

Bulk Materials

In various embodiments, the bulk material employed herein may be in monolithic form.

In various embodiments, the bulk material employed herein may be in particulate form. For example, the chromatographic materials may be in the form of particles, for example, spherical particles, and may have a diameter ranging from 0.25 to 100 μm, for example, ranging from 0.25 μm to 0.5 μm to 1 μm to 2.5 μm to 5 μm to 10 μm to 25 μm to 50 μm to 100 μm (i.e., ranging between any two of the preceding values).

In various embodiments, the bulk material employed herein may be a porous material or a superficially porous material (i.e., a material having a non-porous core region and one or more porous shell regions disclosed over the core region). In various embodiments, the porous or superficially porous material may have a pore size (average pore diameter) ranging from 45 to 3000 Angstroms, for example ranging from 45 to 100 to 250 to 500 to 1000 to 3000 Angstroms, as measured by conventional porosimetry methods. For sub-500 Angstrom pores, the average pore diameter (APD) can be measured using the multipoint $N_2$ sorption method (Micromeritics ASAP 2400; Micromeritics Instruments Inc., Norcross, GA), with APD being calculated from the desorption leg of the isotherm using the BJH method as is known in the art. Hg porosimetry may be used for pores that are 400 Angstrom or greater, as is known in the art.

The bulk material employed herein may be selected, for example, from (a) inorganic materials (e.g., silica, alumina, titania, zirconia, etc.), (b) organic polymeric materials, (c) hybrid inorganic-organic materials, (d) materials having an inorganic core with one or more hybrid inorganic-organic shell layers or with one or more organic polymer shell layers, (e) materials having a hybrid inorganic-organic core with one or more inorganic shell layers or with one or more organic polymer shell layers, (f) materials having an organic polymer core with one or more inorganic shell layers or with one or more hybrid inorganic-organic shell layers, or (g) materials having a hybrid inorganic-organic core with one or more different hybrid inorganic-organic shell layers, among other possibilities.

In various embodiments, the bulk material employed herein may comprise a silicon-based material. For example, the bulk material of the zwitterionic stationary phase may be silica in some embodiments.

As another example, in some embodiments, the bulk material employed herein may comprise a silicon-based inorganic-organic hybrid material that includes inorganic regions in which the material comprises silicon atoms having four silicon-oxygen bonds and hybrid regions in which the material comprises silicon atoms having one or more silicon-oxygen bonds and one or more silicon-carbon bonds. In some cases, the hybrid regions may comprise a substituted or unsubstituted alkylene, alkenylene, alkynylene or arylene moiety bridging two or more silicon atoms. For example, the hybrid regions may comprise a substituted or unsubstituted $C_1$-$C_{18}$ alkylene, $C_2$-$C_{18}$ alkenylene, $C_2$-$C_{18}$ alkynylene or $C_6$-$C_{18}$ arylene moiety bridging two or more silicon atoms. In particular embodiments, the hybrid regions may comprise a substituted or unsubstituted $C_1$-$C_6$ alkylene moiety bridging two or more silicon atoms, including methylene, dimethylene or trimethylene moieties bridging two silicon atoms. In particular embodiments, the hybrid regions comprises may comprise $\equiv Si-(CH_2)_n-Si\equiv$ moieties, where n is an integer, and may be equal to 1, 2, 3, 4 or more.

In various embodiments, the silicon-based inorganic-organic hybrid bulk material may be formed by hydrolytically condensing one or more silane compounds, which typically include (a) one or more silane compounds of the formula $SiZ_1Z_2Z_3Z_4$, where $Z_1$, $Z_2$, $Z_3$ and $Z_4$ are independently selected from Cl, Br, I, $C_1$-$C_4$ alkoxy, $C_1$-$C_4$ alkylamino, and $C_1$-$C_4$ alkyl, although at most three of $Z_1$, $Z_2$, $Z_3$ and $Z_4$ can be $C_1$-$C_4$ alkyl, for example, tetraalkoxysilanes, including tetra-$C_1$-$C_4$-alkoxysilanes such as tetramethoxysilane or tetraethoxysilane, alkyl-trialkoxysilanes, for example, $C_1$-$C_4$-alkyl-tri-$C_1$-$C_4$-alkoxysilanes, such as methyl triethoxysilane, methyl trimethoxysilane, or ethyl triethoxysilane, and dialkyl-dialkoxysilanes, for example, $C_1$-$C_4$-dialkyl-di-$C_1$-$C_4$-alkoxysilanes, such as dimethyl diethoxysilane, dimethyl dimethoxysilane, or diethyl diethoxysilane, among many other possibilities and/or (b) one or more compounds of the formula Si $Z_1Z_2Z_3$-R—$SiZ_4Z_5Z_6$, where $Z_1$, $Z_2$ and $Z_3$ are independently selected from Cl, Br, I, $C_1$-$C_4$ alkoxy, $C_1$-$C_4$ alkylamino, and $C_1$-$C_4$ alkyl, although at most two of $Z_1$, $Z_2$ and $Z_3$ can be $C_1$-$C_4$ alkyl, where $Z_4$, $Z_5$ and $Z_6$ are independently selected from Cl, Br, I, $C_1$-$C_4$ alkoxy, $C_1$-$C_4$ alkylamino, and $C_1$-$C_4$ alkyl, although at most two of $Z_4$, $Z_5$ and $Z_6$ can be $C_1$-$C_4$ alkyl, where R is an organic radical, for example, selected from $C_1$-$C_{18}$ alkylene, $C_2$-$C_{18}$ alkenylene, $C_2$-$C_{18}$ alkynylene or $C_6$-$C_{18}$ arylene groups, for example, $C_1$-$C_4$ alkylene in various embodiments. Examples include bis(trialkoxysilyl)alkanes, for instance, bis(tri-$C_1$-$C_4$-alkoxysilyl)$C_1$-$C_4$-alkanes such as bis(trimethoxysilyl)methane, bis(trimethoxysilyl)ethane, bis(triethoxysilyl)methane, and bis(triethoxysilyl)ethane, among many other possibilities.

In some embodiments, silicon-based inorganic-organic hybrid bulk material may be formed by hydrolytically condensing one or more alkoxysilane compounds. Examples of alkoxysilane compounds include, for instance, tetraalkoxysilanes (e.g., tetramethoxysilane (TMOS), tetraethoxysilane (TEOS), etc.), alkylalkoxysilanes such as alkyltrialkoxysilanes (e.g., methyl trimethoxysilane, methyl triethoxysilane (MTOS), ethyl triethoxysilane, etc.) and bis (trialkoxysilyl)alkanes (e.g., bis(trimethoxysilyl)methane, bis(trimethoxysilyl)ethane, bis(triethoxysilyl)methane, bis (triethoxysilyl)ethane (BTE), etc.), as well as combinations of the foregoing. In certain of these embodiments, silicon-based inorganic-organic hybrid materials may be prepared from two alkoxysilane compounds, for example, a tetraalkoxysilane such as TMOS or TEOS and an alkylalkoxysilane such as MTOS or a bis(trialkoxysilyl)alkane such as BTEE. When BTEE is employed, the resulting materials are organic-inorganic hybrid materials, which are sometimes referred to as ethylene bridged hybrid (BEH) materials and can offer various advantages over conventional silica, including improved chemical and mechanical stability. One particular BEH material can be formed from hydrolytic condensation of TEOS and BTEE.

Further inorganic-organic hybrid materials and methods for forming inorganic-organic hybrid particles described in U.S. Pat. No. 6,686,035B2, which is hereby incorporated by reference.

In various embodiments, the bulk material employed herein may comprise a hydrolytically condensed alkenyl-functionalized organosilane monomer, thereby providing the bulk material with alkenyl-functionalized groups from which organic polymerization can proceed from the bulk material, specifically, polymerization of one or more zwitterionic monomers such as those described below to form covalently attached zwitterionic polymers as described below.

Specific examples of alkenyl-functionalized organosilane monomers include 3-(trimethoxysilyl)propyl methacrylate (also so known as 3-methacryloxypropyltrimethoxysilane, or MAPTMOS), methacryloxypropyltriethoxysilane, methacryloxypropyltrichlorosilane, vinyltriethoxysilane (VTES), vinyltrimethoxy silane, N-(3-acryloxy-2-hydroxypropyl)-3-aminopropyltriethoxysilane, (3-acryloxypropyl)trimethoxysilane, O-(methacryloxyethyl)-N-(triethoxysilylpropyl) urethane, N-(3-methacryl oxy-2-hydroxypropyl)-3 aminopropyltriethoxysilane, methacryloxymethyltriethoxysilane, methacryloxymethyltrimethoxysilane, methacryloxypropylmethyldiethoxysilane, methacryloxypropylmethyldimethoxysilane, methacryloxypropyltris (methoxyethoxy)silane, 3-(N-styrylmethyl-2-aminoethylamino)propyltrimethoxysilane hydrochloride, among others.

In some embodiments, a concentration of silanol groups at a surface of a given silicon-based material may be reduced by reaction with one or more suitable organosilane compounds, for example, one or more silane compounds of the formula $SiZ_7Z_8Z_9Z_{10}$, where $Z_7$, $Z_8$, $Z_9$ and $Z_{10}$ are independently selected from Cl, Br, I, $C_1$-$C_{18}$ alkyl, $C_2$-$C_{18}$ alkenyl, $C_2$-$C_{18}$ alkynyl or $C_6$-$C_{18}$ aryl, wherein at least one and at most three of $Z_7$, $Z_8$, $Z_9$ and $Z_{10}$ is $C_1$-$C_{18}$ alkyl, $C_2$-$C_{18}$ alkenyl, $C_2$-$C_{18}$ alkynyl or $C_6$-$C_{18}$ aryl. In some embodiments, at least one and at most three of $Z_7$, $Z_8$, $Z_9$ and $Z_{10}$ is $C_1$-$C_4$ alkyl. In certain embodiments, silanol groups at a surface of the silicon-based bulk materials may be reduced in concentration by reaction with a haloalkylsilane compound selected from a chlorotrialkylsilane, a dichlorodialkylsilane or a trichloroalkylsilane, such as chlorotrimethylsilane, trimethylchlorosilane or dimethyldiclorosilane.

As previously noted, in various embodiments, the bulk material employed herein may comprise an organic polymer material. In some of these embodiments, the bulk material may comprise an organic copolymer that comprises residues of at least one hydrophobic organic monomer and residues of at least one hydrophilic organic monomer. Organic polymer materials commonly contain residual radical-polymerizable unsaturated surface moieties (e.g., ethylenyl moieties, vinyl moieties, methacryloxy moieties, or acryloxy moieties, etc.), from which polymerization of one or more zwitterionic monomers can proceed.

In certain embodiments, the hydrophilic organic monomer may be selected from organic monomers having an amide group, organic monomers having an ester group, organic monomers having a carbonate group, organic monomers having a carbamate group, organic monomers having a urea group, organic monomers having a hydroxyl group, and organic monomers having nitrogen-containing heterocyclic group, among other possibilities. Specific examples of hydrophilic organic monomers include, for example, 2-vinylpyridine, 3-vinylpyridine, 4-vinylpyridine, N-vinylpyrrolidone, N-vinyl-piperidone, N-vinyl caprolactam, lower alkyl acrylates (e.g., methyl acrylate, ethyl acrylate, etc.), lower alkyl methacrylates (e.g., methyl methacrylate, ethyl methacrylate, etc.), vinyl acetate, acrylamide or methacrylamide, hydroxypolyethoxy allyl ether, ethoxy ethyl methacrylate, ethylene glycol dimethacrylate, or diallyl maleate. In particular embodiments, the hydrophilic organic monomer may be a monomer having the following formula,

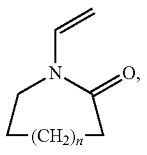

where n ranges from 1-3 (i.e., N-vinyl pyrrolidone, N-vinyl-2-piperidinone or N-vinyl caprolactam).

In certain embodiments, the hydrophobic organic monomer of the organic copolymer may comprise a $C_2$-$C_{18}$ olefin monomer and/or a monomer comprising a $C_6$-$C_{18}$ monocyclic or multicyclic carbocyclic group (e.g., a phenyl group, a phenylene group, naphthalene group, etc.). Specific examples of hydrophobic organic monomers include, for example, monofunctional and multifunctional aromatic monomers such as styrene and divinylbenzene, monofunctional and multifunctional olefin monomers such as ethylene, propylene or butylene, polycarbonate monomers, ethylene terephthalate, monofunctional and multifunctional fluorinated monomers such as fluoroethylene, 1,1-(difluoroethylene), tetrafluoroethylene, chlorotrifluoroethylene, hexafluoropropylene, perfluoropropylvinylether, or perfluoromethylvinylether, monofunctional or multifunctional acrylate monomers having a higher alkyl or carbocyclic group, for example, monofunctional or multifunctional acrylate monomers having a $C_6$-$C_{18}$ alkyl, alkenyl or alkynyl group or a $C_6$-$C_{18}$ saturated, unsaturated or aromatic carbocyclic group, monofunctional or multifunctional methacrylate monomers having a higher alkyl or carbocyclic group, for example, monofunctional or multifunctional methacrylate monomers having a $C_6$-$C_{18}$ alkyl, alkenyl or alkynyl group or a $C_6$-$C_{18}$ saturated, unsaturated or aromatic carbocyclic group, among others. In certain embodiments, DVB 80 may be employed, which is an organic monomer mixture that comprises divinylbenzene (80%) as well as a mixture of ethyl-styrene isomers, diethylbenzene, and can include other isomers as well.

In certain embodiments, the organic copolymer may comprise residues of multifunctional hydrophobic organic monomer such as divinylbenzene and/or a multifunctional hydrophilic organic monomer, such as ethylene glycol dimethacrylate, methylene bisacrylamide or allyl methacrylate, in order to provide crosslinks in the organic copolymer.

In certain embodiments, the organic copolymer may comprise residues of n-vinyl pyrrolidone or n-vinyl caprolactam as a hydrophilic organic monomer residue and residues of divinylbenzene as a hydrophobic organic monomer residue.

Such copolymers may be formed using various methods of free radical polymerization well known in the art. Particles may be formed, for example, as described in U.S. Patent Pub. Nos. 2012/0248033 and 2012/0248033, which are hereby incorporated by reference.

As previously indicated, residual unsaturated groups in the organic polymer bulk material may provide a basis from which organic polymerization can proceed from the bulk material. For example, polymerization of one or more zwitterionic monomers such as those as described below may be used to form covalently attached zwitterionic polymers.

Zwitterionic Surface Groups

As noted above, in some embodiments, the zwitterionic stationary phase may comprise (i) a bulk material (such as those previously described) and (ii) zwitterionic surface groups which comprise a positively charged moiety and a negatively charged moiety.

In various embodiments, the positively charged moiety is a weak anion-exchange moiety such as a primary, secondary or tertiary amine moiety or a strong anion-exchange moiety such as a quaternary amine moiety. In certain of these embodiments, the positively charged moiety may be an acyclic quaternary amine or a cyclic quaternary amine moiety such as a pyridinium moiety or a quinolinium moiety.

In various embodiments, the negatively charged moiety is a weak cation-exchange moiety such as a carboxylate moiety or a strong cation-exchange moiety such as a sulfonate moiety or a phosphate moiety.

In some embodiments, the zwitterionic surface groups may be forming by adsorbing a zwitterionic compound to a surface of the bulk material.

In some embodiments, the zwitterionic stationary phase may comprise a non-polymeric zwitterionic species covalently linked to a surface of the bulk material.

In some embodiments, the zwitterionic stationary phase may comprise a zwitterionic polymer that comprises one or more zwitterionic monomer residues covalently linked to a surface of the bulk material.

The zwitterionic monomer residues are residues of a zwitterionic monomer (i.e., a monomer that contains a positively charged moiety and a negatively charged moiety such as those previously described). In some embodiments, the zwitterionic species may contain, on average, 1-20 zwitterionic monomer residues, 1-10 zwitterionic monomer residues, 1-6 zwitterionic monomer residues, 1-3 zwitterionic monomer residues, or 1-2 zwitterionic monomer residues.

In various embodiments, the zwitterionic polymer that comprises one or more zwitterionic monomer residues is covalently linked to the surface of the bulk material via a radically polymerizable unsaturated moiety such as an ethylenyl moiety, a vinyl moiety, a methacryloxy moiety, or an acryloxy moiety, among others, that is present at the surface of the bulk material and is able to participate in radical polymerization of one or more zwitterionic monomers (e.g., zwitterionic monomers having radically polymerizable unsaturated functional group), thereby forming the zwitterionic polymer. For example, as previously indicated, in some embodiments, the zwitterionic polymer is covalently linked to the surface of the bulk material through a residue of an organosilane monomer (e.g., an alkenyl-functionalized organosilane monomer) that enables radical polymerization of one or more zwitterionic monomers to proceed at the surface of the bulk material, thereby forming the covalently linked zwitterionic polymer. In some embodiments, the molar ratio of the zwitterionic monomer residues to the organosilane monomer residues may range from 0.5 to 20, for example, ranging from 0.5 to 0.75 to 1.0 to 1.5 to 2 to 5 to 10 to 15 to 20. Such polymerization reactions may be conducted under conditions known in the radical polymerization art.

In various embodiments, the positively charged moiety is separated from the negatively charged moiety within the zwitterionic monomer residue by a $C_1$-$C_{12}$ alkyl group, more typically, a $C_2$-$C_5$ alkyl group and, in some specific embodiments, a $C_3$ alkyl group.

In various embodiments, the zwitterionic monomer residue comprises an amide, urea moiety or an ester moiety.

In various embodiments, the zwitterion of the zwitterionic monomer residue is (a) directly connected to the carbon backbone of the zwitterionic polymer (e.g., a nitrogen atom of a tertiary or quaternary amine directly linked to the carbon backbone), (b) linked to the carbon backbone of the zwitterionic polymer through a $C_1$-$C_{12}$ alkyl group, more particularly, through a $C_2$-$C_5$ alkyl group, (c) linked to the carbon backbone of the zwitterionic polymer through an amide group, for instance, through a $C_1$-$C_{12}$ alkyl amide group, more particularly, through a $C_2$-$C_5$ alkyl amide group, where the alkyl group may be attached to the carbon backbone (and the amide group may be located in the middle or at the end of the alkyl group) or wherein the amide group may be attached to the carbon backbone, (d) linked to the carbon backbone of the zwitterionic polymer through a urea group, for instance, through a $C_1$-$C_{12}$ alkyl urea group, more particularly, through a $C_2$-$C_5$ alkyl urea group, and/or (e) linked to the carbon backbone of the zwitterionic polymer through an ester group, for instance, through a $C_1$-$C_{12}$ alkyl ester group, more particularly, through a $C_2$-$C_5$ alkyl ester group, where the alkyl group may be attached to the carbon backbone (and the ester group may be located in the middle or at the end of the alkyl group) or wherein the ester group may be attached to the carbon backbone.

In some embodiments, the zwitterion of the zwitterionic monomer residue may be oriented such that the positively charged moiety of the zwitterion is closest to the carbon backbone of the zwitterionic polymer. In some embodiments, the zwitterion of the zwitterionic monomer residue may be oriented such that the negatively charged moiety of the zwitterion is closest to the carbon backbone of the zwitterionic polymer.

In various embodiments, the surface concentration of the zwitterionic monomer residues ranges from 0.5 $\mu mol/m^2$ to 40 $\mu mol/m^2$, for example, ranging from 0.5 $\mu mol/m^2$ to 1 $\mu mol/m^2$ to 2 $\mu mol/m^2$ to 5 $\mu mol/m^2$ to 10 $\mu mol/m^2$ to 20 $\mu mol/m^2$ to 40 $\mu mol/m^2$ (i.e., ranging between any two of these values).

Examples of radically polymerizable zwitterionic monomers that that may be used to form the zwitterionic polymers of the present disclosure may be selected from the following, among others: Dimethyl(methacryloyloxyethyl) ammonium propane sulfonate, Dimethyl(methacryloylaminopropyl) ammonium propane sulfonate, 3-[(3-Acrylamidopropyl)dimethylammonio]propanoate, 4-[(3-Methacrylamidopropyl) dimethylammonio]butane-1-sulfonate, 3-[(3-Acrylamidopropyl)dimethylammonio]propane-1-sulfonate, 1-(3-

Sulfopropyl)-2-Vinylpyridinium Betaine, Pyridinium, 2-ethenyl-1-(2-hydroxy-3-sulfopropyl)-, inner salt, Pyridinium, 2-(2-phenylethenyl)-1-(3-sulfopropyl)-, inner salt, Quinolinium, 2-(2-phenylethenyl)-1-(3-sulfopropyl)-, inner salt, Pyridinium, 2-[(1E)-2-[4-(dimethylamino)phenyl]ethenyl]-1-(3-sulfopropyl)-, inner salt, Pyridinium, 2-[2-[4-(dimethylamino)phenyl]ethenyl]-1-(3-sulfopropyl)-, inner salt, Pyridinium, 2-[(1E)-2-[4-(diethylamino)phenyl]ethenyl]-1-(3-sulfopropyl)-, inner salt, 1-Propanaminium, 2-hydroxy-N,N-dimethyl-N-[3-[(2-methyl-1-oxo-2-propen-1-yl) amino]propyl]-3-sulfo-, inner salt, 1-Propanaminium, N,N-diethyl-2-hydroxy-N-[3-[(2-methyl-1-oxo-2-propen-1-yl) amino]propyl]-3-sulfo-, inner salt, 1-Propanaminium, 3-azido-N-methyl-N-[3-[(2-methyl-1-oxo-2-propen-1-yl) amino]propyl]-N-(3-sulfopropyl)-, inner salt, 5-Hexen-1-aminium, N,N-dimethyl-N-[3-(methylamino)propyl]-3-sulfo-, inner salt, 1-Propanaminium, N,N-dimethyl-N-[3-[(1-oxo-3-buten-1-yl)amino]propyl]-3-sulfo-, inner salt, 1-Propanaminium, 2-hydroxy-N,N-dimethyl-N-[3-[(1-oxo-2-propen-1-yl)amino]propyl]-3-sulfo-, inner salt, 1-Propanaminium, N,N-dimethyl-N-[3-[[(9Z)-1-oxo-9-hexadecen-1-yl]amino]propyl]-3-sulfo-, inner salt, 1-Propanaminium, N,N-dimethyl-N-[3-[[(9Z)-1-oxo-9-octadecen-1-yl]amino] propyl]-3-sulfo-, inner salt, 1-Propanaminium, N,N-dimethyl-N-[3-[[[(2-methyl-1-oxo-2-propen-1-yl)amino]carbonyl]amino]propyl]-3-sulfo-, inner salt, 1-Propanaminium, N,N-dimethyl-N-[3-[[(13Z)-1-oxo-13-docosen-1-yl]amino] propyl]-3-sulfo-, inner salt, 1-Propanaminium, N,N-dimethyl-N-[3-[[(9Z)-1-oxo-9-docosen-1-yl]amino]propyl]-3-sulfo-, inner salt, 1-Propanaminium, N,N-dimethyl-N-[3-[(1-oxo-13-docosen-1-yl)amino]propyl]-3-sulfo-1-Propanaminium, 2-hydroxy-N, N-dimethyl-N-[3-[(1-oxo-9-decen-1-yl)amino]propyl]-3-sulfo-, inner salt, 1-Propanaminium, N-[3-[[(2Z)-3-carboxy-1-oxo-2-propen-1-yl]amino]propyl]-2-hydroxy-N,N-dimethyl-3-sulfo-, 1-Propanaminium, N-[3-[(3-carboxy-1-oxo-2-propen-1-yl) amino]propyl]-2-hydroxy-N,N-dimethyl-3-sulfo-, 1-Propanaminium, 2-hydroxy-N,N-dimethyl-N-[3-[[(9E)-1-oxo-9-dodecen-1-yl]amino]propyl]-3-sulfo-, inner salt, 1-Propanaminium, 2-hydroxy-N,N-dimethyl-N-[3-[(1-oxo-9-dodecen-1-yl)amino]propyl]-3-sulfo-, inner salt, 1-Propanaminium, 2-hydroxy-N,N-dimethyl-N-[3-[[(9Z)-1-oxo-9-hexadecen-1-yl]amino]propyl]-3-sulfo-, inner salt, 1-Propanaminium, 2-hydroxy-N,N-dimethyl-N-[3-[(1-oxo-9-octadecen-1-yl)amino]propyl]-3-sulfo-, inner salt, 1-Propanaminium, 2-hydroxy-N,N-dimethyl-N-[3-[(1-oxo-13-docosen-1-yl)amino]propyl]-3-sulfo-, inner salt, 1-Propanaminium, 2-hydroxy-N,N-dimethyl-N-[3-[[(9E, 12E,15E)-1-oxo-9,12,15-heptadecatrien-1-yl]amino]propyl]-3-sulfo-, 1-Propanaminium, 3,3'-[(1-oxo-2-propen-1-yl) imino]bis[N,N-dimethyl-N-(3-sulfopropyl)-, bis(inner salt), 2-Butanaminium, N,N'-[[(1-oxo-2-propen-1-yl)imino] di-3,1-propanediyl]bis [N,N-dimethyl-4-sulfo-, bis(inner salt), 1-Propanaminium, 3-[[[(6-isocyanatohexyl)amino] carbonyl]amino]-N,N-dimethyl-N-(3-sulfopropyl)-, inner salt, 1-Propanaminium, 3-[[[[4-[(4-isocyanatocyclohexyl) methyl]cyclohexyl]amino]carbonyl]amino]-N,N-dimethyl-N-(3-sulfopropyl)-, inner salt, 1-Propanaminium, 3-[[[[(5-isocyanato-1,3,3-trimethylcyclohexyl)methyl]amino] carbonyl]amino]-N,N-dimethyl-N-(3-sulfopropyl)-, inner salt.

Additional zwitterionic monomers that are able to participate in radical polymerization may be generated from known zwitterionic compounds by functionalizing such compounds with an radically polymerizable unsaturated functional group to allow for participation in polymerization reactions. Such zwitterionic compounds include the following among others: 1-Propanaminium, 3-[(4-heptylbenzoyl) amino]-N,N-dimethyl-N-(3-sulfopropyl)-, inner salt, 1-Propanaminium, 3-[(4-decylbenzoyl)amino]-N,N-dimethyl-N-(3-sulfopropyl)-, inner salt, 1-Propanaminium, N,N-dimethyl-N-[3-[[4-(octyloxy)benzoyl]amino]propyl]-3-sulfo-, inner salt, 1-Propanaminium, N-ethyl-2-hydroxy-N-methyl-N-[3-[(4-octylbenzoyl)amino]propyl]-3-sulfo-, inner salt, 1-Propanaminium, 3-[(hydroxymethyl)(3-pyridinylcarbonyl)amino]-N,N-dimethyl-N-(3-sulfopropyl)-, inner salt, 1-Propanaminium, 3-amino-N-[3-[[(3',6'-dihydroxy-3-oxospiro[isobenzofuran-1(3H),9'-[9H]xanthen]-5-yl)carbonyl]amino]propyl]-N-methyl-N-(3-sulfopropyl)-, inner salt, 1-Propanaminium, 3-[(4-carboxy-1-oxobutyl) amino]-N-[3-[[(3',6'-dihydroxy-3-oxospiro[isobenzofuran-1(3 H),9'-[9H]xanthen]-5-yl)carbonyl]amino]propyl]-N-methyl-N-(3-sulfopropyl)-, inner salt, 1,3-Prop anediaminium, N1,N1,N3,N3-tetramethyl-N1,N3-bis(3-sulfopropyl)-, bis(inner salt), 1-Propanaminium, 3-(dimethylamino)-N,N-dimethyl-N-(3-sulfopropyl)-, inner salt, 1-Propanaminium, N-(2-hydroxyethyl)-3-[(2-hydroxyethyl) methylamino]-N-methyl-N-(3-sulfopropyl)-, inner salt, 1-Propanaminium, 2-hydroxy-N-[3-[(2-hydroxyethyl)methylamino]propyl]-N,N-dimethyl-3-sulfo-, inner salt, 1-Propanaminium, N-[3-(formylamino)propyl]-2-hydroxy-N,N-dimethyl-3-sulfo-, inner salt, 1-Propanaminium, 3-[(3-mercapto-1-oxopropyl)amino]-N,N-dimethyl-N-(3-sulfopropyl)-, inner salt, 1,3-Propanediaminium, N1,N3-bis (2-hydroxy-3-sulfopropyl)-N1,N1,N3,N3-tetramethyl-, bis (inner salt), 1-Propanaminium, 3-amino-N,N-dimethyl-N-(3-sulfopropyl)-, inner salt, 1-Propanaminium, 3-amino-N-(3-aminopropyl)-N-methyl-N-(3-sulfopropyl)-, inner salt, 1-Propanaminium, 3-isocyano-N,N-dimethyl-N-(3-sulfopropyl)-, inner salt, 1-Propanaminium, N-(3-aminopropyl)-2-hydroxy-N,N-dimethyl-3-sulfo-, inner salt, 1-Propanaminium, 3-(chloroamino)-2-hydroxy-N,N-dimethyl-N-(3-sulfopropyl)-, inner salt, 1-Propanaminium, 3-[(3-carboxy-1-oxopropyl)amino]-N, N-dimethyl-N-(3-sulfopropyl)-, inner salt, 1-Propanaminium, N,N-dimethyl-N-[3[(1-oxo-12-thioxotridecyl)amino]propyl]-3-sulfo-, inner salt, 1-Propanaminium, 3-[(4-carboxy-1-oxobutyl) amino]-N,N-dimethyl-N-(3-sulfopropyl)-, inner salt, and 1-Propanaminium, 3-[[5-(1,2-dithiolan-3-yl)-1-oxopentyl]amino]-N,N-dimethyl-N-(3-sulfopropyl)-, inner salt.

Column Materials

Suitable construction materials for the chromatographic columns of the present disclosure include inorganic materials, for instance, metals such as stainless steel and ceramics such as glass, as well as synthetic polymeric materials such as polyethylene, polypropylene, polyether ether ketone (PEEK), and polytetrafluoroethylene, among others.

In various embodiments, an internal diameter of the chromatographic columns ranges from 2.0 to 3.0 mm. In various embodiments, an internal length of the chromatographic column ranges from 25 to 75 mm.

In various embodiments, the chromatographic columns for use in the present disclosure include those in which an inner surface of the chromatographic column comprise an alkylsilyl coating. In some embodiments, the alkylsilyl coating has a thickness ranging from 100 Å to 1600 Å, among other values.

In some embodiments, the alkylsilyl coating has the Formula I:

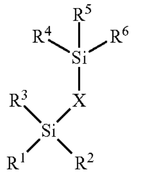

wherein $R^1$, $R^2$, $R^3$, $R^4$, $R^5$, and $R^6$ are each independently selected from $(C_1-C_6)$alkoxy, —NH$(C_1-C_6)$alkyl, —N($(C_1-C_6)$alkyl$)_2$, OH, $OR^A$, and halo; $R^A$ represents a point of attachment to the interior surfaces of the fluidic system; at least one of $R^1$, $R^2$, $R^3$, $R^4$, $R^5$, and $R^6$ is $OR^A$; and X is $(C_1-C_{20})$alkyl, —O$[(CH_2)_2O]_{1-20}$—, —$(C_1-C_{10})$[NH(CO)NH$(C_1-C_{10})]_{1-20}$—, or —$(C_1-C_{10})$[alkylphenyl$(C_1-C_{10})$alkyl$]_{1-20}$—.

In particular embodiments, X is $(C_2-C_{10})$alkyl, more particularly, ethyl. In particular embodiments, $R^1$, $R^2$, $R^3$, $R^4$, $R^5$, and $R^6$ are each independently selected from methoxy, chloro and $OR^A$, where at least one of $R^1$, $R^2$, $R^3$, $R^4$, $R^5$, and $R^6$ is $OR^A$. In particular embodiments, the alkylsilyl coating of Formula I is hydrolyzed bis(trichlorosilyl)ethane or bis(trimethoxysilyl)ethane.

In some embodiments, the an inner surface of the chromatographic column comprises a second alkylsilyl coating in direct contact with the alkylsilyl coating of Formula I, the second alkylsilyl coating having the Formula II:

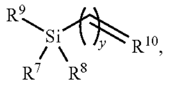

wherein $R^7$, $R^8$, and $R^9$ are each independently selected from —NH$(C_1-C_6)$alkyl, $(C_1-C_6)$alkoxy, $(C_1-C_6)$alkyl, $(C_1-C_6)$ alkenyl, OH, and halo; $R^{10}$ is selected from $(C_1-C_6)$alkyl, —$OR^B$, —[O$(C_1-C_3)$alkyl$]_{1-10}$O$(C_1-C_6)$alkyl, —[O$(C_1-C_3)$ alkyl$]_{1-10}$OH and phenyl, wherein said $(C_1-C_6)$alkyl is optionally substituted with one or more halo and wherein said phenyl is optionally substituted with one or more groups selected from $(C_1-C_3)$alkyl, hydroxyl, fluorine, chlorine, bromine, cyano, —C(O)$NH_2$, and carboxyl; $R^B$ is —$(C_1-C_3)$alkyloxirane, —$(C_1-C_3)$alkyl-3,4-epoxycyclohexyl, or —$(C_1-C_4)$alkylOH; the hashed bond to $R^{10}$ represents an optional additional covalent bond between $R^{10}$ and the carbon bridging the silyl group to form an alkene, provided y is not 0; and y is an integer from 0 to 20.

In particular embodiments, y is an integer from 2 to 9. In particular embodiments, $R^{10}$ is methyl, and $R^7$, $R^8$, and $R^9$ are each ethoxy or chloro. In particular embodiments, the alkylsilyl coating of Formula II is hydrolyzed (3-glycidyloxypropyl)trimethoxysilane, n-decyltrichlorosilane, trimethylchlorosilane, trimethyldimethyaminosilane, methoxy-polyethyleneoxy(1-10) propyl trichlorosilane, or methoxy-polyethyleneoxy(1-10) propyl trimethoxysilane. In particular embodiments, the alkylsilyl coating of Formula II is hydrolyzed (3-glycidyloxypropyl)trimethoxysilane.

In some embodiments, the inner surface of the chromatographic column further comprises an alkylsilyl coating having the Formula III,

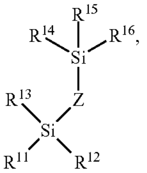

in direct contact with the alkylsilyl coating of Formula I, wherein $R^{11}$, $R^{12}$, $R^{13}$, $R^{14}$, $R^{15}$, and $R^{16}$ are each independently selected from $(C_1-C_6)$alkoxy, —NH$(C_1-C_6)$alkyl, —N($(C_1-C_6)$alkyl$)_2$, OH, and halo; and Z is $(C_1-C_{20})$alkyl, —O$[(CH_2)_2O]_{1-20}$—, —$(C_1-C_{10})$[NH(CO)NH$(C_1-C_{10})$] or —$(C_1-C_{10})$ [alkylphenyl$(C_1-C_{10})$alkyl$]_{1-20}$. In some embodiments, the alkylsilyl coating of Formula III is hydrolyzed bis(trichlorosilyl)ethane or bis(trimethoxysilyl)ethane.

Further coatings suitable for use in the present disclosure are described in US 2019/0086371, which is hereby incorporated by reference.

Example 1

BEH porous hybrid particles were prepared following the method as described in U.S. Pat. No. 6,686,035 and surface modified by techniques known to those skilled in the art. More particularly, anhydrous BEH porous hybrid particles were surface modified with an alkenyl-functionalized organosilane (methacryloxypropyltrichlorosilane) through a reaction in toluene at elevated temperature for 4 h in the presence of a catalyst (diisopropylethylamine). The reaction mixture was cooled, and the particles were isolated, washed, transferred to a clean reaction vessel, heated for 3 h in an aqueous acetone solution (pH 7), cooled, isolated, washed, and dried under vacuum.

Polymerization of a zwitterionic polymer was then conducted from the alkenyl-functionalized surface of the modified BEH particles of the prior paragraph using techniques known to those skilled in the art. More particularly, dimethyl (methacryloylaminopropyl) ammonium propane sulfonate was covalently bonded to the alkenyl-functionalized surface of the surface modified BEH particles of Example 1 by polymerization in the presence of a polymerization initiator in aqueous methanol solution at elevated temperature for 3-20 h. The reaction mixture was then cooled, and the particles were isolated, washed, transferred into a clean reaction vessel, heated in an aqueous solution (pH 2-10), cooled, isolated, washed to neutral pH, and dried under vacuum.

Example 2

Stock solutions and sample concentrations for 13 RNA component compounds, specifically, 4 nucleobases (adenine, cytosine, uracil and guanine), 4 nucleosides (adenosine, cytidine, uridine and guanosine), 4 nucleotides (adenosine monophosphate (AMP), cytidine monophosphate (CMP), uridine monophosphate (UMP) and guanosine monophosphate (GMP)), and ribose phosphate, are shown in Table 2.

TABLE 1

| Compound | Stock Concentration (mg/mL) | Stock Diluent | Analysis Concentration (μg/mL) |
|---|---|---|---|
| Adenine | 1.0 | 50:50 Acetonitrile:Water with 0.1% formic acid | 2.0 |
| Adenosine | 1.0 | 50:50 Acetonitrile:Water with 0.1% formic acid | 2.0 |
| AMP | 1.0 | 50:50 Acetonitrile:Water | 30.0 |
| Cytosine | 1.0 | 50:50 Acetonitrile:Water | 2.0 |
| Cytidine | 1.0 | 50:50 Acetonitrile:Water | 2.0 |
| CMP | 1.0 | 50:50 Acetonitrile:Water | 50.0 |
| Uracil | 1.0 | 50:50 Acetonitrile:Water | 2.0 |
| Uridine | 1.0 | 50:50 Acetonitrile:Water | 2.0 |
| UMP | 1.0 | 50:50 Acetonitrile:Water | 50.0 |
| Guanine | 0.5 | 1:1 Acetonitrile:100 mM KOH* | 2.0 |
| Guanosine | 1.0 | 50:50 Acetonitrile:Water with 0.1% formic acid | 2.0 |
| GMP | 1.0 | 50:50 Acetonitrile:Water | 50.0 |
| Ribose Phosphate | 1.0 | 50:50 Acetonitrile:Water | 50.0 |

*Guanine not soluble in water.

Multiple reaction monitoring (MRM) mass spectrometry conditions were developed by infusing standards into LC flow and comparing to literature values. Results are show in Table 2. Mass spectra were also run as Selected Ion Recording (SIR) with same cone voltages and precursor ions.

TABLE 2

| Compound | Ionization Mode | Precursor Ion (m/z) | Cone Voltage (V) | Product Ions (m/z) | Capillary Voltage (V) |
|---|---|---|---|---|---|
| Adenine | ESI+ | 136.0 | 30 | 119.0 | 20 |
| Adenosine | ESI+ | 268.0 | 30 | 136.0/119.0 | 10/45 |
| AMP | ESI+ | 348.0 | 30 | 136.0/119.0 | 20/55 |
| Cytosine | ESI+ | 112.0 | 30 | 95.0 | 20 |
| Cytidine | ESI+ | 244.0 | 30 | 112.0/95.0 | 15/45 |
| CMP | ESI+ | 324.0 | 30 | 112.0/95.0 | 15/55 |
| Uracil | ESI− | 111.0 | 20 | N/A | N/A |
| Uridine | ESI− | 243.0 | 20 | 200.0/110.0 | 10/15 |
| UMP | ESI− | 323.0 | 20 | 111.0 | 30 |
| Guanine | ESI+ | 152.0 | 30 | 135.0 | 20 |
| Guanosine | ESI+ | 284.0 | 30 | 152.0/135.0 | 15/35 |
| GMP | ESI+ | 364.0 | 30 | 152.0/135.0 | 15/50 |
| Ribose Phosphate* | ESI− | 229.0 | 20 | 97.0 | 15 |

*Also run as SIR with same cone voltage and precursor ion

Liquid chromatography separations and mass spectrometry analyses were run using the following system, with the following columns, under the following conditions.

System: Waters H-Class with CM, CM-AUX, and XEVO™ TQD and Premier Hardware

Columns: Waters BEH™ Amide 2.1×50 mm, 1.7 μm, standard hardware

Example 1 particles; Waters 2.1×50 mm, 1.7 μm, MaxPeak™ Premier hardware

Agilent Poroshell HILIC-z 2.1×50 mm, 1.9 μm, standard hardware

Raptor Polar X 2.1×50 mm, 2.5 μm, standard hardware

Column Temp: 50° C.

Mobile Phase A: Water

Mobile Phase B: Acetonitrile

Mobile Phase D1: 200 mM ammonium formate buffer pH 3.0

Flow Rate: 0.5 mL/min

Gradient: See Table 3 for Initial Gradient

Sample Composition: Acetonitrile:Water (876:124) with 0.1% formic acid

Injection Volume: 0.5 μL

TABLE 3

| Time (min) | % A | % B | % D1 | Aq. Slope (%/min) | Buffer Slope (mM/min |
|---|---|---|---|---|---|
| 0.00 | 0 | 95 | 5 | — | — |
| 10.36 | 15 | 60 | 25 | 3.38 | 3.86 |
| 11.57 | 15 | 60 | 25 | — | — |
| 11.63 | 0 | 95 | 5 | — | — |
| 15.00 | 0 | 95 | 5 | — | — |

Figure 1B:
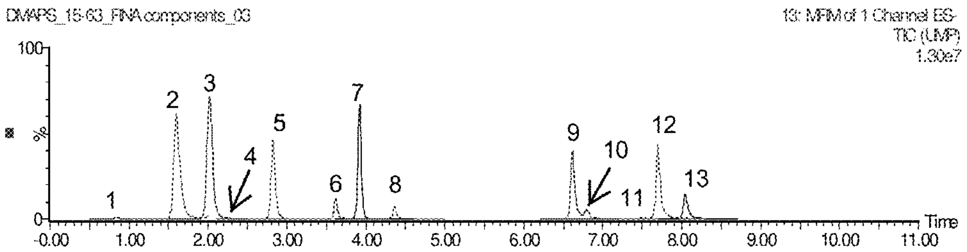
Figure 1C:
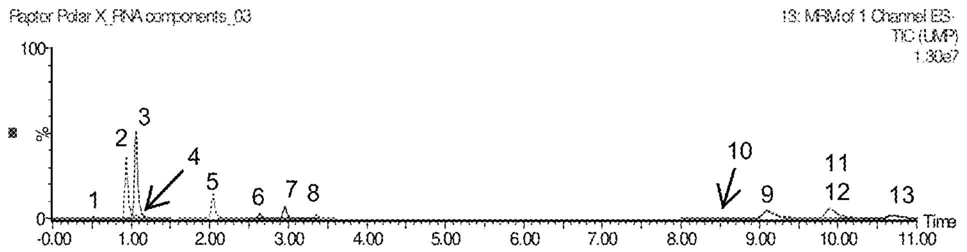
Figure 1D:
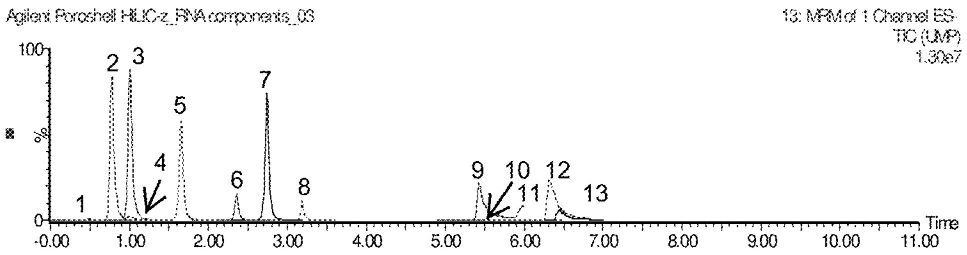

Samples containing the 13 RNA component compounds were separated and analyzed using the above systems and conditions. Chromatograms are shown in FIGS. 1A-1D and 2A-2D. Chromatograms corresponding to separation on the column containing the BEH amide particles are shown in FIG. 1A (linked Y-axis) and FIG. 2A (normalized Y-axis). Chromatograms corresponding to separation on the column containing the Example 1 particles are shown in FIG. 1B (linked Y-axis) and FIG. 2B (normalized Y-axis). Chromatograms corresponding to separation on the column containing the Poroshell HILIC-z particles are shown in FIG. 1C (linked Y-axis) and FIG. 2C (normalized Y-axis). Chromatograms corresponding to separation on the column containing the Raptor Polar X particles are shown in FIG. 1D (linked Y-axis) and FIG. 2D (normalized Y-axis). MS signal comparisons are shown in Table 4. Table 4 also provides the peak ID reference numbers for the 13 RNA components as shown in FIGS. 1A-2D.

TABLE 4

| Compound | Peak ID | ESI Mode | Signal (BEH Amide) | Signal (Example 1) | Signal (Poroshell HILIC-z) | Signal (Raptor Polar X) |
|---|---|---|---|---|---|---|
| Adenine | 2 | ESI+ | 1.29 e7 | 7.96 e6 | 1.09 e7 | 4.64 e6 |
| Adenosine | 3 | ESI+ | 1.28 e7 | 9.26 e6 | 1.15 e7 | 6.67 e6 |
| AMP | 9 | ESI+ | 9.77 e6 | 5.22 e6 | 2.76 e6 | 5.51 e5 |
| Cytosine | 5 | ESI+ | 8.97 e6 | 5.94 e6 | 7.62 e6 | 1.87 e6 |
| Cytidine | 7 | ESI+ | 1.28 e7 | 8.63 e6 | 9.59 e6 | 8.47 e5 |
| CMP | 12 | ESI+ | 6.09 e6 | 5.64 e6 | 3.10 e6 | 7.26 e5 |
| Uracil | 1 | ESI− | 2.22 e5 | 9.94 e4 | 1.05 e5 | 6.66 e4 |
| Uridine | 4 | ESI− | 7.68 e4 | 3.88 e4 | 4.04 e4 | 3.85 e4 |
| UMP | 10 | ESI− | 1.80 e4 | 1.17 e4 | 9.91 e3 | 3.15 e3 |
| Guanine | 6 | ESI+ | 1.46 e6 | 1.53 e6 | 2.04 e6 | 3.55 e5 |
| Guanosine | 8 | ESI+ | 1.47 e6 | 1.00 e6 | 1.49 e6 | 3.06 e5 |
| GMP | 13 | ESI+ | 2.39 e6 | 1.83 e6 | 7.59 e5 | 2.02 e5 |
| Ribose Phosphate | 11 | ESI− | 1.16 e5 | 1.37 e5 | 2.70 e4 | 1.00 e4 |
| Average Signal | | ESI+ | 7.63 e6 | 5.22 e6 | 5.53 e6 | 1.80 e6 |
| Average Signal | | ESI− | 1.08 e5 | 7.17 e4 | 4.56 e4 | 2.96 e4 |

Figure 2A:
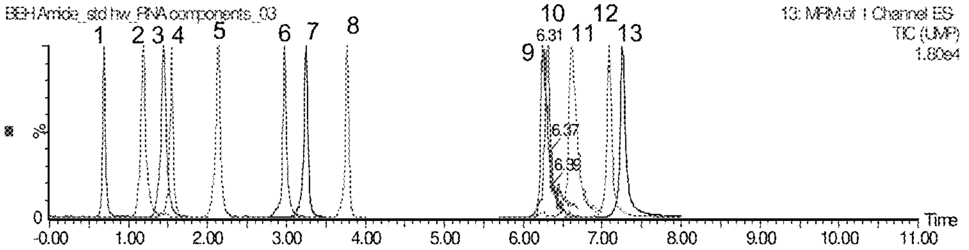
FIGS. 2A-2D are chromatograms corresponding to attempted separations of thirteen different RNA component compounds in a sample, using four different zwitterionic columns, wherein the Y-axes of the chromatograms are normalized. Each compound (Uracil, Adenine, Adenosine, Uridine, Cytosine, Guanine, Cytidine, Guanosine, AMP, UMP, Ribose phosphate, CMP and GMP) is assigned to a peak number (1, 2, 3, 4, 5, 6, 7, 8, 9, 10, 11, 12 and 13) respectively.

As seen from FIGS. 1A and 2A, the BEH amide column was unable to resolve the AMP/UMP pair. Also the adenosine/uridine critical pair are very closely eluting. Additionally, the peak shape for AMP is poor and leads to interferences with ribose phosphate (tailing of AMP co-elutes with ribose phosphate).

Figure 2B:
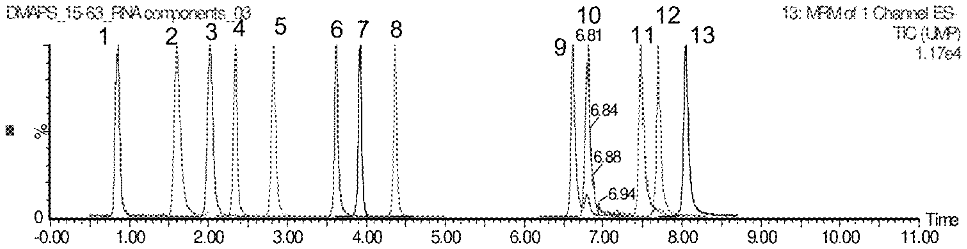

As seen from FIGS. 1B and 2B, the column containing the Example 1 particles shows much better peak shape. AMP/UMP are fully resolved; adenosine/uridine are fully resolved. Ribose phosphate is eluted without interference from other analytes. A sharp peak shape was obtained for phosphorylated compounds. The Example 1 particles also show higher retentivity compared to BEH Amide, even though the separation is a gradient separation. The improvements were believed to be not only due to the differing particles from BEH amide column, but also due to the $C_2$-alkylsilyl surface coating found on inner surfaces of the Premier hardware.

Figure 2C:
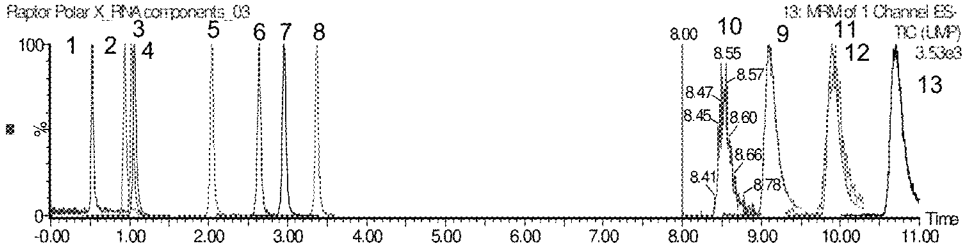

As seen from FIGS. 1C and 2C, the Raptor Polar X column shows higher retention for phosphorylated compounds, but lower retention for other compounds. Peak shapes on this column are poor with all of the phosphorylated compounds tailing significantly. This column was unable to resolve adenine/adenosine/uridine as well as ribose phosphate/CMP. An elution order change of AMP/UMP and adenosine/uridine, with UMP and uridine eluting before the AMP and adenosine compounds, was also noted. There was also poor ionization for most compounds compared to BEH Amide and the Example 1 particles.

Figure 2D:
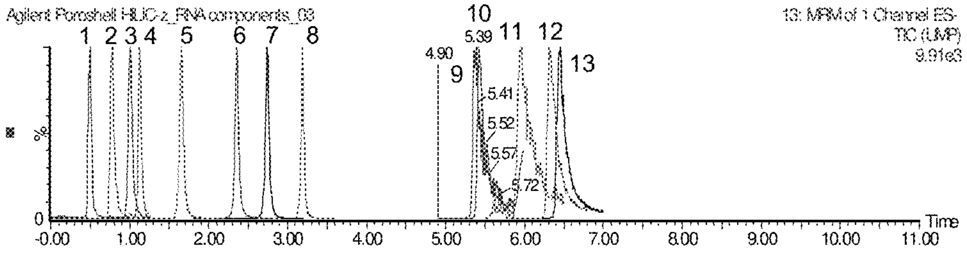

As seen from FIGS. 1D and 2D, the Poroshell HILIC-z column was unable to separate AMP/UMP or CMP/GMP. Additionally, the phosphorylated compounds have poor peak shape (tailing), likely due to conventional hardware being used. The Poroshell HILIC-z column also had lowest retentivity of materials tested.

What is claimed is:

1. A method comprising: (a) loading a sample fluid comprising a plurality of nucleic acid component compounds onto a chromatographic column comprising a zwitterionic stationary phase contained inside the column, wherein the zwitterionic stationary phase is a particulate stationary phase and comprises (i) a bulk material comprising an ethylene bridged hybrid (BEH) material, and (ii) zwitterionic surface groups covalently linked to the bulk material or a zwitterionic polymer covalently linked to a surface of the bulk material; (b) flowing a mobile phase through the chromatographic column over a time period thereby forming an eluent in which at least some of the plurality of the nucleic acid component compounds are separated from each other, the mobile phase comprising a polar aprotic solvent, a protic solvent, and a volatile buffer salt, wherein flowing the mobile phase comprises varying a ratio of the protic solvent to the polar aprotic solvent over at least a portion of the time period and varying an ionic strength of the volatile buffer salt over at least a portion of the time period.

2. The method of claim 1, further comprising performing mass spectrometry analysis of the eluent.

3. The method of claim 1, wherein the zwitterionic surface groups comprise a positively charged moiety and a negatively charged moiety.

4. The method of claim 1, wherein the zwitterionic polymer comprises one or more monomer residues that comprise an amide or urea moiety, a positively charged moiety and a negatively charged moiety.

5. The method of claim 1, wherein an inner surface of the chromatographic column comprises a $(C_2\text{-}C_{10})$alkylsilyl coating.

6. The method of claim 1, wherein the nucleic acid component compounds comprise RNA component compounds.

7. The method of claim 6, wherein the RNA component compounds are selected from nucleobases, nucleosides, nucleotides and ribose phosphate.

8. The method of claim 1, wherein the protic solvent is selected from water, methanol, ethanol, 1-propanol, 2-propanol, t-butanol and blends thereof.

9. The method of claim 1, wherein the protic solvent is water.

10. The method of claim 1, wherein the polar aprotic solvent is selected from acetonitrile, acetone, tetrahydrofuran, methylene chloride, ethyl acetate, N,N-dimethylformamide, dimethyl sulfoxide, dimethyl ether, and blends thereof.

11. The method of claim 1, wherein the polar aprotic solvent is acetonitrile.

12. The method of claim 1, wherein the volatile buffer salt comprises an organic acid anion and a cation selected from an ammonium cation and an amine cation.

13. The method of claim 12, wherein the organic acid anion is selected from formate, acetate, propionate, butyrate, oxalate, malonate, succinate, maleate, glutarate, glycolate, lactate, malate, citrate, gluconate and combinations thereof.

14. The method of claim 1, wherein flowing the mobile phase comprises combining varying relative amounts of (a) a first mobile phase component comprising an aqueous solution of the volatile buffer salt and (b) a second mobile phase component comprising the polar aprotic solvent.

15. The method of claim 1, wherein flowing the mobile phase comprises combining varying relative amounts of (a) a first mobile phase component comprising an aqueous solution of the volatile buffer salt, (b) a second mobile phase component comprising the polar aprotic solvent, and (c) a third mobile phase component comprising the protic solvent.

16. The method of claim 1, wherein mass spectrometry analysis is performed on the eluent and wherein the mass spectrometer is operated in positive ion mode.

17. The method of claim 1, wherein mass spectrometry analysis is performed on the eluent and wherein the mass spectrometer is operated in negative ion mode.

18. The method of claim 1, wherein the sample fluid comprises the plurality of nucleic acid component compounds, a protic solvent, a polar aprotic solvent, and an organic acid.

19. The method of claim 1, wherein the sample fluid comprises the plurality of nucleic acid component compounds, water, acetonitrile and formic acid.

* * * * *